United States Patent [19]

Hodnett

[11] Patent Number: 4,748,697
[45] Date of Patent: Jun. 7, 1988

[54] FACE MASK WITH INTERCHANGEABLE LENSES

[76] Inventor: Jack L. Hodnett, Rte. 3, Box 792, Deville, La. 71328

[21] Appl. No.: 30,084

[22] Filed: Mar. 26, 1987

[51] Int. Cl.$^4$ .............................................. A61F 9/02
[52] U.S. Cl. ........................................................ 2/438
[58] Field of Search ................... 2/438, 434, 435, 422, 2/8, 9, 10, 424

[56] References Cited

U.S. PATENT DOCUMENTS

| | | | |
|---|---|---|---|
| 2,119,439 | 5/1938 | Parmelee | 2/8 X |
| 2,592,805 | 4/1952 | Hutchinson | 2/8 X |
| 2,886,819 | 5/1959 | Uphoff | 2/438 |
| 4,428,081 | 1/1984 | Smith | 2/438 |
| 4,542,538 | 9/1985 | Moretti et al. | 2/438 |

*Primary Examiner*—Peter Nerbun
*Attorney, Agent, or Firm*—John M. Harrison

[57] ABSTRACT

A face mask which is characterized by a soft rubber or plastic cowl provided with a track insert having pair of tracks spanning an open lens window for receiving a transparent lens slidably mounted in the tracks and closing the lens window. In a preferred embodiment, the lens is a tear-away lens connected at a perforated interface to the next one of several additional lenses wound in end-to-end relationship in a roll, which roll is located inside a canister attached to the track insert of the face mask. Each lens is individually, selectively and sequentially extended through a slot in the canister and through the parallel lens tracks to a track lip projecting from the opposite side of the track insert, when the preceding lens is damaged or coated so as to adversely affect visibility and is removed from the lens tracks. When the damaged lens is slidably extended from the lens tracks in the face mask for removal, a second lens is unrolled from the canister and slidably positioned over the lens window and the damaged lens is torn from the leading edge of the newly positioned lens at the perforated interface between the lenses.

22 Claims, 1 Drawing Sheet

U.S. Patent  Jun. 7, 1988  4,748,697
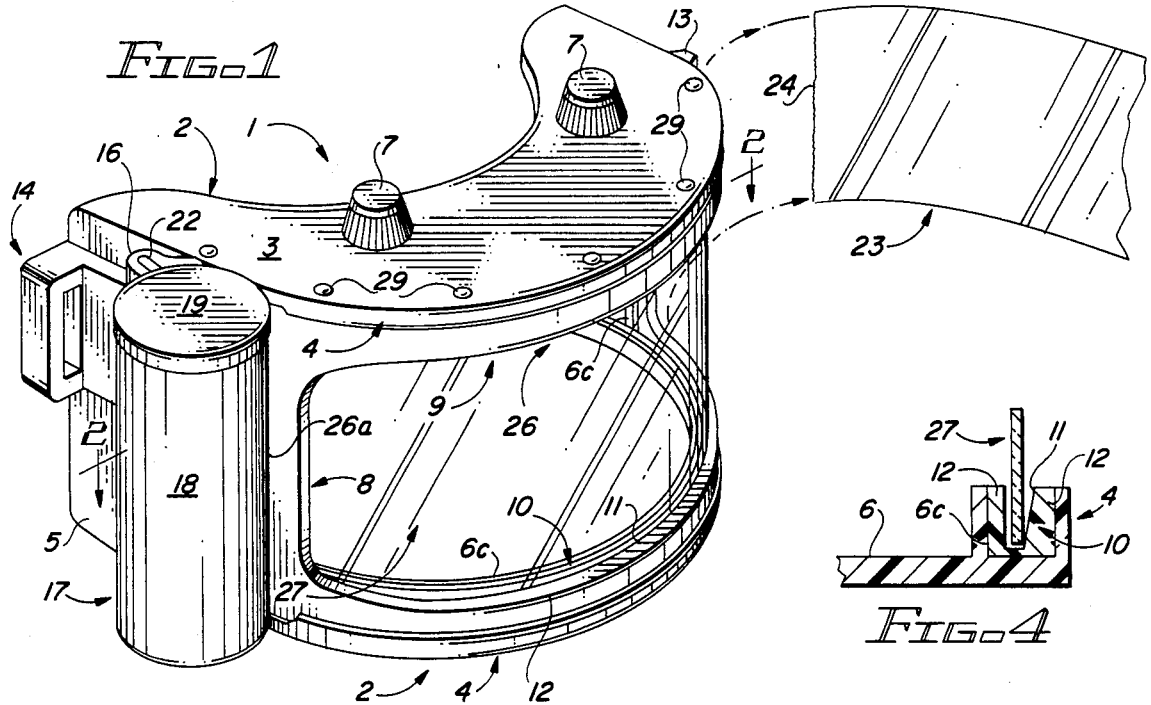
Fig. 1
Fig. 4
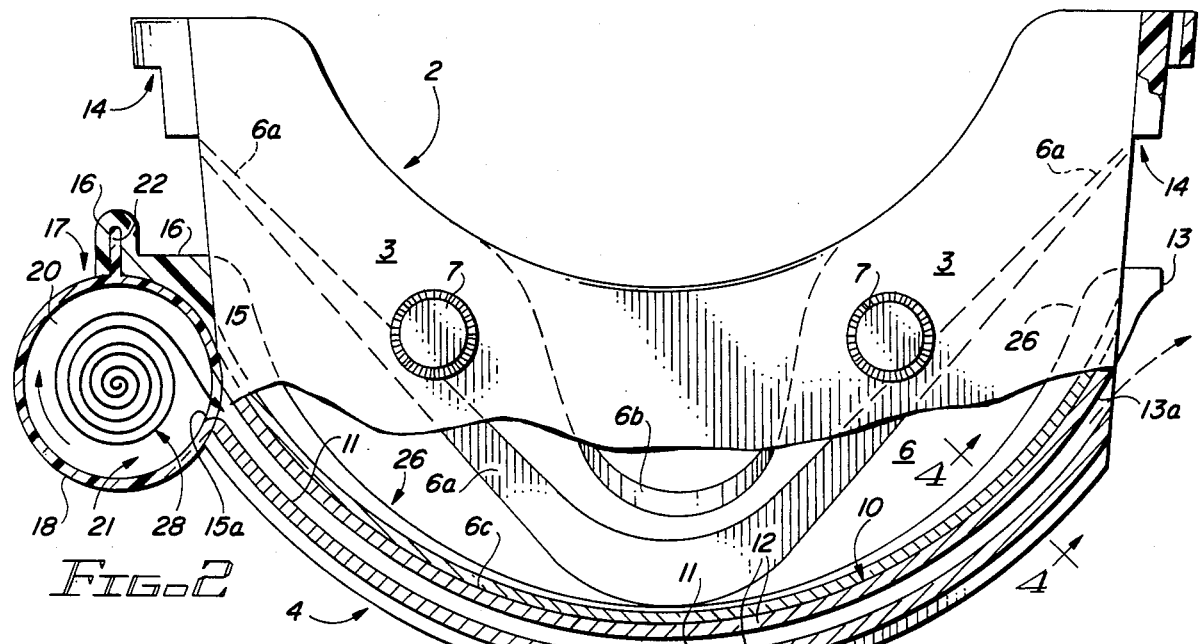
Fig. 2
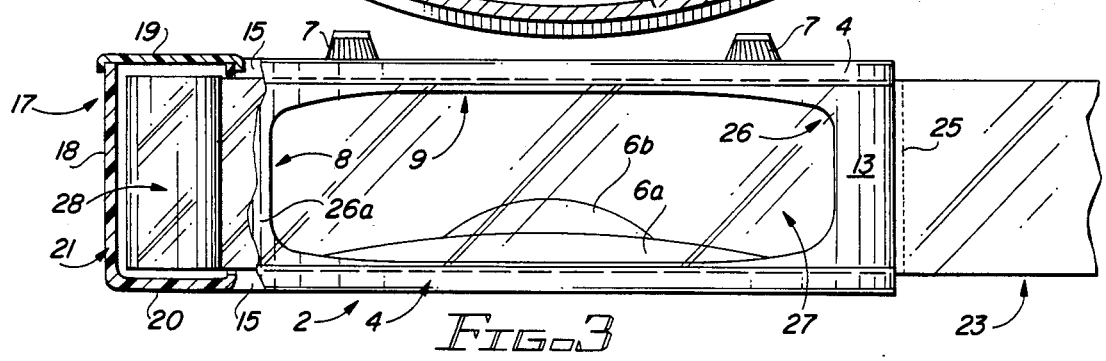
Fig. 3

FACE MASK WITH INTERCHANGEABLE LENSES

BACKGROUND OF THE INVENTION

1. Field of the Invention

This invention relates to masks, single lens goggles and helmets used for painting, sandblasting and other activities requiring that the head, face or eyes be covered and protected while working. More particularly, the invention relates to a protective mask, helmet or single lens goggles having interchangeable lenses, and specifically, to a face mask which is characterized by a track insert having an open lens window bordered by a pair of lens tracks and mounted in a flexible cowl. The parallel lens tracks are designed to receive a flexible, transparent lens which is attached to one in a series of adjacent lenses in end to end, rolled and perforated relationship and loaded in a canister which is removable attached to the track insert. Each lens can be projected across the open lens window by inserting the leading edge thereof through a slot in the canister and sliding the lens through the tracks bordering the lens window. When so positioned, the lens can be used until it is either obscured by paint or scratched or until visibility through the lens is otherwise limited or obscured. The leading edge of the lens can then be grasped at the track lip of the track insert and the lens pulled completely from the lens window to a line of perforation, at which time the adjacent and connected lens is extended from the canister and located in functional position replacing the first lens. The damaged first lens can then be torn from the adjacent new lens at the track lip along the perforations and discarded. In a preferred embodiment, the flexible cowl is removably secured to the track insert by pins inserted in registering openings located in the cowl and the track insert.

One of the problems which exists in industries that deal with painting, sandblasting and other activities which require the use of protective face masks, goggles and helmets with lenses, is that of periodically damaging or obscuring the lens, thereby requiring that the protective equipment be discarded. Face masks which are commonly used to protect the eyes are typically shaped from a soft rubber or plastic material and the lens is usually constructed of a soft, flexible plastic or similar material which is easily abraded, fogged or scratched to obscure the vision of the wearer. Alternatively, in such operations as painting, paint can quickly settle on the lens and obscure the vision of the wearer, thereby requiring that the mask be discarded. While the cost of these masks is not usually excessive, the cost of the entire mask is generally significantly higher than the cost of replacing the lens itself.

2. Description of the Prior Art

Various types of industrial masks, goggles and helmets are well known in the art for such industrial applications as painting, sandblasting and other operations requiring shielding of the eyes and/or protection of the face.

The most simple eyeshields commonly used in industry are one-piece, transparent goggles and eyeglasses which are provided with plastic frames and shatterproof lenses for general application in an environment where eye hazards exist. Other eyeshields such as face masks and goggles which are commonly constructed of a soft rubber or plastic material with plastic lenses, are well known in the art and are used in such applications as painting, certain shop applications and other industrial applications requiring eye protection. More complex helmets and hoods fitted with lenses for viewing the work area are also known in the art for such applications as welding and sandblasting, where both the eyes and face must be protected. Helmets of this nature are typified by the Clemco Industries "Widespan" helmet, model WSH, which is characterized by an extra large window mounted in a helmet that carries a hood or cape for use in such operations as sandblasting. The "Widespan" helmet includes multiple, easily replaceable, peel-off acetate lenses which are attached over a fixed outer lens or window, in order to assure good visibility during the course of the job. As each acetate lens becomes dirty, pitted or is otherwise rendered unusable, it is peeled from the underlying lens to expose the clean lens. If the peel-off acetate lenses are not used, then the underlying helmet lens or window must be replaced if it is damaged. A similar helmet marketed by Clemco Industries is known as the "Apollo" helmet, which is constructed with a double shell to permit air circulation throughout the entire head area. The window viewing area is slanted downwardly to allow clear vision to the lower part of the work area and to increase the overall field of vision. Multiple, peel-off acetate lenses allow convenient replacement of frosted, pitted or otherwise damaged outside lens.

One of the problems which exists with prior art face masks, goggles and helmet systems wherein the lens can be easily obscured by paint, frosting, pitting or other damage, is the requirement of replacing the lens in the helmet or discarding the goggles or face mask when such an event occurs. For example, in the case of the Clemco "Widespan" helmet and the "Apollo" helmet, at least one peel-off acetate lenses must be applied to the underlying base lend or window, in order to facilitate a means of periodically replacing the exposed and damaged lens. Accordingly, if the operator fails to remember to place the multiple peel-on acetate lenses over the underlying permanent lens, the permanent lens itself can be damaged, thus necessitating replacement and perhaps causing costly down-time on the job. Furthermore, the peeling off of successive layers of acetate or other plastic-type lenses can be laborious and time consuming and each of these lenses must be provided with an adhesive, in order to secure successive layers of the lenses to the underlying base lens and to each other. Another problem which may become apparent with regard to the use of thin, peel-off acetate lenses, is that of pitting the underlying lens or lenses when the exposed lens is damaged by sandblasting or other industrial operations.

Accordingly, it is an object of this invention to provide a new and improved face mask, single lens goggles or helmet that is provided with interchangeable, transparent lenses which are carried in a canister attached to the face mask, goggles or helmet and are successively slidably replaced in the lens window of the face mask, goggles or helmet as the exposed, damaged lenses are individually removed.

Another object of this invention is to provide a new and improved face mask having a linear interchangeable lens capability, which face mask is provided with a canister fitted with multiple, flexible, rolled lenses attached in end-to-end, perforated relationship, which lenses are adapted for sequential feeding through a slot in the canister and through a pair of tracks spanning the lens window of the face mask, in order to successively and slidably remove damaged lenses and slide new lenses into position over the lens window in a single operation, as deemed necessary.

Yet another object of this invention is to provide a new and improved face mask or single lens goggles formed of soft rubber, plastic, or other desirable material and provided with a canister and a lens window bordered by a pair of parallel, spaced tracks, which canister contains multiple, flexible, rolled lenses mounted in perforated, end-to-end relationship, for slidably and sequentially extending through a slot in the canister and the tracks and covering the lens window, such that each can be slidably replaced when damaged or obscured, by removing the damaged or obscured lens from the lens window, simultaneously slidably replacing that lens with an adjacent lens from the canister and tearing the old lens from the new one along the perforations.

Still another object of this invention is to provide a new and improved facemask with interchangeable transparent lenses, which face mask includes a cowl constructed or rubber, plastic or other suitable material and provided with air vents on the top thereof, a rigid track insert removably attached to the cowl and a canister removably mounted on one end of the track insert, which canister contains multiple plastic lenses that are rolled inside the canister and are attached in perforated, end-to-end relationship, for sequentially extending in parallel tracks located in the track insert and across the lens window of the face mask. Damaged or obscured lenses are successively removed from the lens window, while simultaneously extending a second adjacent lens from the canister across the lens window in functional configuration. The removed lens is then torn from the new lens along the perforated interface.

SUMMARY OF THE INVENTION

These and other objects of the invention are provided in a new and improved face mask having linearly interchangeable transparent lenses, which face mask is characterized by flexible, shaped cowl fitted with a more rigid track insert having an open lens window spanned by a top and bottom track for receiving the first one of a strip of several flexible, transparent lenses provided in rolled, perforated, end-to-end relationship in a canister attached to the track insert. As each lens is damaged or visually obscured and requires replacement, it is slidably displaced from the top and bottom track and the lens window, to pulls the adjacent lens through a slot in the canister and the top and bottom track and across the lens window. The first lens is then severed from the second lens at a perforation to provide a means for replacing lenses in the face mask or goggles.

BRIEF DESCRIPTION OF THE DRAWING

The invention will be better understood by reference to the accompanying drawing, wherein:

FIG. 1 is a perspective view of a preferred embodiment of the face mask of this invention, with the bottom cowl segment removed for clarity;

FIG. 2 is a sectional view, taken along line 2—2 of the face mask illustrated in FIG. 1;

FIG. 3 is a front elevation, partially in section, of the face mask illustrated in FIGS. 1 and 2; and FIG. 4 is a sectional view of the bottom lens track and front cowl segments, taken along line 4—4 in FIG. 2.

DESCRIPTION OF THE PREFERRED EMBODIMENTS

Referring initially to FIGS. 1 and 2 of the drawing, the face mask of this invention is generally illustrated by reference numeral 1. The face mask 1 is characterized by a cowl 2, which is shaped to define a flat top cowl segment 3, a curved front cowl segment 4, a side cowl segment 5, a bottom cowl segment 6 and a rear cowl segment 6c, illustrated in FIG. 2. A pair of air vents 7 are provided in the top cowl segment 3, in order to ventilate the face mask 1. A generally cylindrically-shaped canister 17, provided with a longitudinally-projecting canister plate 22, is secured to the slotted canister mount flange 16 extending from the side plate 26a, which shapes the left-hand side of a track insert 26, inserted in the cowl 2. The track insert 26 is substantially rigid in construction and includes a curved top lens track 9 and a curved bottom lens track 10, spaced from the top lens track 9, which combine with the side plate 26a and track lip 13, to define a lens window 8. In a most preferred embodiment, the canister mount flange 16 is fitted with a slot, which tightly receives the canister plate 22, in order to removably, but securely secure the canister 17 to the track insert 26. The canister 17 is further characterized by a cylindrical canister barrel 18, closed by a canister top 19 and a canister bottom 20, as illustrated in FIG. 2. The side cowl segments 5 of the face mask 1 are further provided with a pair of oppositely disposed, spaced strap brackets 14, for securing the ends of a head band or strap (not illustrated), in order to secure the face mask 1 on the face of a user. As further illustrated in FIGS. 1 and 2 the top cowl segment 3 is configured to fit tightly around the forehead of a user, while the bottom cowl segment 6 is provided with a bottom ridge 6a and a nose ridge 6b, which are shaped to receive the nose of the user and to fit snugly around the cheeks of the user.

Referring now to FIGS. 1 and 4 of the drawings, the top lens track 9 of the track insert 26 is secured between the top portion of the front cowl segment 4 and the rear cowl segment 6c, while the corresponding bottom lens track 10 is sandwiched between the bottom segment of the front cowl segment 4 and the rear cowl segment 6c. Furthermore, the top lens track 9 and bottom lens track 10 span the lens window 8 and are each characterized by a tapered track slot 11, defined by facing track flanges 12, as illustrated in FIG. 4. As heretofore described, the top lens track 9 and the bottom lens track 10 are joined to the side plate 26a at the left hand side of the track insert 26 (as the face mask 1 is viewed in FIG. 1) and a track feed opening 15 is provided in the side plate 26a, as illustrated in FIG. 2. The track feed opening 15 lies adjacent to and registers with a canister slot 15a, provided longitudinally in the canister barrel 18 of the canister 17. The opposite ends of the top lens track 9 and bottom lens track 10 are connected at the track lip 13, provided with a lip opening 13a, located at the right hand side of the track insert 26, as the face mask 1 is viewed in FIG. 1. As further illustrated in FIG. 2, multiple, flexible, rolled lenses 28 are provided in the canister interior 21 of the canister barrel 18 for sequential feeding through the top lens track 9 and bottom lens track 10 to close the lens window 8. The rolled lenses 28 can be constructed of an acetate, polycarbonate or plastic material which is transparent and is sufficiently flexible to facilitate rolling into a spring-like configuration, according to the knowledge of those skilled in the art.

Furthermore, the rolled lenses 28 can be clear or tinted or shaded, including specially shaded for welding purposes, as desired, for specific industrial applications. In a most preferred embodiment of the invention the lenses 23 are constructed of polycarbonate or other impact-resistant material having a thickness of about 20 mils.

Referring now to FIGS. 1–4 of the drawing and initially to FIGS. 2–4, a new lens 27 is extended across the lens window 8 from the rolled lens 28 stored in the canister interior of the canister barrel 18, by initially fitting the leading edge of the new lens 27 through the canister slot 15a in the canister barrel 18 and the track feed opening 15 in the track insert 26. This action fits the top and bottom edges of the new lens 27 in the top lens track 9 and the bottom lens track 10, respectively. The new lens 27 is then extruded along the top lens track 9 and the bottom lens track 10 until the leading edge thereof projects through the lip opening 13a, located on the opposite side of the track insert 26, and lies adjacent the track lip 13, as illustrated in FIG. 2. The new lens 27 is thusly securely located in the top lens track 9 and the bottom lens track 10 of the track insert 26 and completely covers the lens window 8, as illustrated in FIG. 1. The face mask 1 can then be used for the desired industrial application until the new lens 27 becomes scratched, abraded, fogged or coated and the face mask 1 is rendered unsuitable for its intended purpose. When this occurs, instead of discarding the face mask 1, the leading edge of the new lens 27 lying adjacent the track lip 13 is grasped and the new lens 27 if pulled from the top track 9 and the bottom lens track 10, as illustrated in FIG. 1, where it is designated as an old lens 23. This action in turn pulls a second new lens 27 from the rolled lenses 28 located inside the canister barrel 18 of the canister 17, into the position in the top 35 lens track 9 and bottom lens track 10 which was formally occupied by the old lens 23. When the leading edge of the new lens 27 reaches the track lip 13 as illustrated in FIG. 3, the old lens 23 is torn from the new lens 27 along the lens perforation line 25, to define the jagged perforations 24, as illustrated in FIG. 1. In this manner, each of the rolled lenses 28 located in the canister interior 21 of the canister barrel 18 is selectively, sequentially and slidably positioned in the top lens track 9 and the bottom lens track 10 covering the lens window 8, by successive removal of the respective preceding old lens 23 and tearing the old lens 23 at each lens perforation line 25

It will be appreciated by those skilled in the art that the face mask of this invention offers a welcomed alternative to the current technology of placing multiple layers of acetate or other lenses over a base lens. This advantage is apparent under circumstances where multiple, stacked lenses are abraded or damaged such that multiple layers of the lenses are rendered unfit for the intended purpose. Since the rolled lenses 28 are safely stored in the canister 17 of the face mask 1 of this invention for sequentially and slidably positioning in the lens window 8, they are protected from damage when the face mask 1 is in use. Furthermore, each new lens 27 can be quickly, easily and slidably placed in position covering the lens window 8 as needed, by simply tearing the preceding damaged old lens 23 from the leading edge of the corresponding new lens 27 along the lens perforation line 25, as heretofore described.

It will be further appreciated by those skilled in the art that the rolled lenses 28 can be fabricated of substantially any transparent material, including acetate and polycarbonate materials, in non-exclusive particular, which materials are flexible and may be rolled into a spring-like configuration for fitting into the canister 17, according to the knowledge of those skilled in the art. Furthermore, the rolled lenses 28 can be sealed inside the canister 17 such that the canister top 19 and canister bottom 20 cannot be easily opened, thereby requiring that a new canister 17 be inserted in the canister mount flange 16 when the rolled lenses 28 are depleted from the old canister 17. Also, under circumstances where the material of construction used to construct the face mask 1 has a limited life in the particular industrial application under consideration, the canister 17 can be fixedly attached to the track insert 26 on the face mask 1 and sealed to enclose a selected number of rolled lenses 28 which correspond to the average life of the face mask 1.

It will be still further appreciated that the canister 17 can be constructed with a canister barrel 18 of sufficient diameter to contain a selected number of rolled lenses 28, depending upon the particular application desired and the face mask 1 can be constructed of any desired size and shape. It is only necessary that the distance between the lens perforation lines 25 in the rolled lenses 28 be sufficient to span the lens window 8.

It is understood that while the face mask 1 of this invention is most preferably characterized by a separate track insert 26 which removably fits in a flexible cowl 2, the track insert 26 can also be permanently attached to, or molded integrally with the cowl 2, as desired.

While the preferred embodiments of the invention have been described above, it will be recognized and understood that various modifications may be made therein and the appended claims are intended to cover all such modifications which may fall within the spirit and scope of the invention.

Having described my invention with the particularity set forth above, what is claimed is:

1. A face mask with interchangeable lenses, comprising a substantially flexible cowl shaped to substantially cover at least the eyes of a user; an open window provided in said cowl; a pair of spaced, curved, substantially rigid tracks removably carried by said cowl, said tracks spanning said window in spaced relationship for slidably receiving said lenses in end-to-end relationship and positioning said lenses sequentially in said window; and canister means carried by one end of said tracks for enclosing said lenses in rolled configuration and dispensing said lenses in said window responsive to manual and sequential extension of said lenses along said tracks.

2. The face mask of claim 1 further comprising perforations provided in said lenses in spaced relationship to define a separate lens between each set of said perforations.

3. The face mask of claim 1 further comprising pin means extending through said cowl and said tracks for removably securing said tracks to said cowl.

4. The face mask of claim 1 wherein said cowl means further comprises a substantially flexible cowl adapted to receive and mount said tracks and said flange means in removable relationship and a track lip joining said tracks at the opposite end of said tracks from said flange means and a lip slot provided in said track lip for receiving the leading edge of said lenses when said lenses are individually extended in said tracks and cover said window.

5. The face mask of claim 4 further comprising perforations provided in said lenses in spaced relationship to define a separate lens between each set of said perforations.

6. The face mask of claim 5 further comprising pin means extending through said cowl and said tracks for removably securing said tracks to said cowl.

7. The face mask of claim 1 further comprising at least one air vent provided in said cowl for ventilating said face mask.

8. The face mask of claim 7 further comprising:
(a) pin means extending through said cowl and said tracks for removably securing said tracks to said cowl; and
(b) a track lip joining said tracks at the opposite end of said tracks from said flange means and a lip slot provided in said track lip for receiving the leading edge of said lenses when said lenses are individually extended in said tracks and cover said window.

9. The face mask of claim 8 further comprising a pair of strap brackets carried by said cowl in spaced relationship and a head strap having both ends secured to said strap brackets, respectively, for securing said face mask on the head of a user.

10. A face mask with interchangeable lenses, comprising flexible cowl means; front cowl segments provide along the top and bottom edges of said flexible cowl means in spaced, facing relationship; a pair of strap brackets carried by said flexible cowl means for adjustably securing a head strap to said flexible cowl means; substantially rigid track insert means inserted in said flexible cowl means and a pair of curved tracks disposed in said track insert means in spaced relationship, said tracks adapted to removably engage said front cowl segments of said cowl means and said tracks further defining a lens window therebetween; a plurality of pin means extending through said cowl means and said tracks in spaced relationship, for removably securing said tracks to said cowl means; a generally cylindrically-shaped canister carried by said track insert means and a longitudinal slot provided in said canister; and a plurality of lenses provided in said canister in rolled relationship, whereby said lenses are extendible in sequence through said longitudinal slot in said canister and slidably in said tracks to close said lens window.

11. The face mask of claim 10 further comprising perforations provided in said lenses in spaced relationship to define a separate lens between each set of said perforations.

12. The face mask of claim 10 further comprising perforations provided in said lenses in spaced relationship to define a separate lens between each set of said perforations.

13. The face mask of claim 10 further comprising flange means joining said tracks at one end of said track insert and fastening means extending from said canister, said flange means adapted to removably receive said fastening means and secure said canister to said track insert.

14. The face mask of claim 13 further comprising a track lip joining said tracks at the opposite end of said track insert from said flange means and a lip slot provided in said track lip for receiving the leading edge of said lenses when said lenses are individually extended in said tracks and cover said window.

15. The face mask of claim 12 further comprising:
(a) flange means joining said tracks at one end of said track insert and fastening means extending from said canister, said flange means adapted to removably receive said fastening means and secure said canister to said track insert; and
(b) a track lip joining said tracks at the opposite end of said track insert from said flange means and a lip slot provided in said track lip for receiving the leading edge of said lenses when said lenses are individually extended in said tracks and cover said window.

16. A face mask with interchangeable lenses, comprising a flexible cowl, a pair of front cowl segments having cowl slots disposed in spaced, facing relationship provided along the top and bottom edges of said flexible cowl; a pair of strap brackets carried by said flexible cowl for adjustably securing a head strap to said flexible cowl; a substantially rigid track insert having a pair of spaced, curved tracks removably inserted in said cowl slots in spaced relationship, said tracks defining a lens window therebetween; a cylindrically-shaped canister carried by said track insert and a longitudinal canister slot provided in said canister; and a plurality of lenses provided in said canister in rolled relationship, whereby said lenses are linearly extended in sequence through said longitudinal canister slot and slidably in said tracks to close said lens window.

17. A face mask of claim 16 further comprising perforations provided in said lenses in spaced relationship to define a separate lens between each set of said perforations.

18. The face mask of claim 16 further comprising a plurality of pins extending through said cowl and said tracks in spaced relationship, for removably securing said tracks to said cowl.

19. The face mask of claim 16 further comprising:
(a) perforations provided in said lenses in spaced relationship to define a separate lens between each set of said perforations; and
(b) a plurality of pins extending through said cowl and said tracks in spaced relationship, for removably securing said tracks to said cowl.

20. The face mask of claim 16 further comprising flange means joining said tracks at one end of said track inset and fastening means extending from said canister, said flange means adapted to removably receive said fastening means and secure said canister to said track insert.

21. The face mask of claim 20 further comprising a track lip joining said tracks at the opposite end of said track insert from said flange means and a lip slot provided in said track lip for receiving the leading edge of said lenses when said lenses are individually extended in said tracks and cover said window.

22. The face mask of claim 19 further comprising:
(a) flange means joining said tracks at one end of said track insert and fastening means extending from said canister, said flange means adapted to removably receive said fastening means and secure said canister to said track insert; and
(b) a track lip joining said tracks at the opposite end of said track insert from said flange means and a lip slot provided in said track lip for receiving the leading edge of said lenses when said lenses are individually extended in said tracks and cover said window.

* * * * *